United States Patent [19]
Stephen et al.

[11] Patent Number: 5,401,239
[45] Date of Patent: Mar. 28, 1995

[54] ELECTROMOTIVE TREATMENT OF CATHETER-RERELATED INFECTIONS

[75] Inventors: Robert L. Stephen, Salt Lake City, Utah; Cino Rossi, Rome; Silvio Eruzzi, Mantova, both of Italy

[73] Assignee: Physion s.r.l., Mirandola, Italy

[21] Appl. No.: 29,701

[22] Filed: Mar. 11, 1993

[51] Int. Cl.⁶ .............................................. A61N 1/30
[52] U.S. Cl. .......................... 604/21; 604/20; 604/96; 128/639
[58] Field of Search ............. 604/20, 21, 52, 53, 604/76, 171, 163, 265, 266; 128/639, 640, 642, 643, 644, 654, 656, 658, DIG. 21; 607/115, 116, 133

[56] References Cited

U.S. PATENT DOCUMENTS

| | | | |
|---|---|---|---|
| 4,411,648 | 10/1983 | Davis et al. | 604/21 |
| 4,479,795 | 10/1984 | Mustacich et al. | 604/53 |
| 5,154,165 | 10/1992 | Elliott et al. | 604/20 X |

FOREIGN PATENT DOCUMENTS

| | | | |
|---|---|---|---|
| 0869778 | 10/1981 | U.S.S.R. | 604/20 |
| 9116945 | 11/1991 | WIPO | 604/96 |

Primary Examiner—John D. Yasko
Assistant Examiner—V. Alexander
Attorney, Agent, or Firm—Jacobson & Johnson

[57] ABSTRACT

A method of treating recalcitrant indewelling catheter-associated infections including the following procedures: inserting into the lumen of the catheter, a primary electrode whose uninsulated distal section is of a spiral or filamentous configuration physically contacting the internal surface of the catheter; positioning and sealing a secondary electrode-receptacle on the skin area around the exit site of the catheter and around an external section of the catheter so as to form a conical container for holding liquids; infusion of a solution of antimicrobial drugs through the catheter; instilling a solution of antimicrobial drugs into the secondary electrode-receptacle; and applying a voltage differential between the primary and secondary electrodes, in which an electric field is applied to the internal and external surfaces of the catheter, and this field both disrupts hitherto priviledged sites for microorganisms on the surfaces of the catheter and drives antimicrobial drugs into these same surfaces.

10 Claims, 2 Drawing Sheets

ELECTROMOTIVE TREATMENT OF CATHETER-RERELATED INFECTIONS

BACKGROUND OF THE INVENTION

1. Field of the Invention

The present invention relates to the treatment of catheter-related infections. In particular, this invention describes the use of electric fields in association with electromotive administration of antimicrobial drugs for sterilization of indwelling catheters.

2. Description of Prior Art

Catheters (tubes) of many shapes and dimensions are inserted into numerous bodily areas. For the purpose of this invention, catheters are divided conveniently by function: infusion; drainage; infusion and drainage.

Infusion Catheters: The great majority of catheters and lines used for infusion purposes are inserted into the venous system and may also be classified by their functional lifetimes.

Every day there occur a large number of minor operations and/or investigative procedures during which intravenous (iv) cannulae are inserted, both to administer treatments and as a safety measure. Usually the lines are removed in under 12 hours and the patients are discharged that same day. For almost all major surgical operations, iv infusions into peripheral veins are maintained for 1-3 days. Occasionally following really major surgery or because of complications or a specific requirement for iv drugs, the lines remain sited in peripheral veins for up to a week.

With the increasing average age of general population, the increasing incidence of immunosuppressive regimens for transplant operations, the increasing incidence of immunosuppressive diseases (primarily due to HIV) and the increasingly drastic anticancer treatments being employed, iv access is now utilised more and more frequently for increasingly longer periods of time: weeks, months and sometimes years for Total Parenteral Nutrition (TPN). An unremarkable sight in major medical centers is that of patients receiving iv anticancer drugs (most of which suppress, and some almost obliterate, bodily defence mechanisms) and multiple antimicrobial drugs via the same line, the latter being used to combat opportunistic infections caused by the former.

The above examples are but two of many and they lead to an issue pertinent to this invention. Peripheral veins used for access sites are prone to thrombosis, so the great majority of long term iv access catheters are inserted with terminal ends sited in one of the great veins, usually the subclavian vein. These central line catheters are longer, of greater diameter and more flexible than catheters used for peripheral veins.

Drainage Catheters: Following many surgical operations, drainage tubes are inserted into the operative regions in order to prevent localized collections of fluid which may form abscesses. This is a time-proven safety measure but these tubes do breach the skin and infectious organisms enter the breach, although usually not deeply enough to cause severe illness. The tubes, which are required to drain everything from bile to blood clot are of many shapes but all result in a relatively large breach in the skin, usually 1 cm—3 cm in diameter.

Another type of drainage catheter in common usage and pertinent to this invention is the bladder catheter. Occasionally placed directly through the abdominal wall, it is usually inserted via the urethra. Indwelling, long term catheters are employed frequently as a means of bladder drainage in patients with neuromuscular dysfunction of the bladder neck, and sometimes in paraplegic and quadriplegic persons.

Infusion and Drainage: Occasionally infusion catheters are used to draw blood and the bladder catheter is often employed as a means of lavaging the bladder.

However, the two types of catheters that are truly representative of infusion/drainage of large volumes of fluid are those used for hemodialysis and peritoneal dialysis.

Most people treated by hemodialysis possess a surgically created A-V fistula for blood access but, until the fistula "matures", blood access is most often obtained by insertion of subclavian catheters which are maintained in position for about one month. Persons treated by long term peritoneal dialysis (PD) require a "permanent" catheter placed in the peritoneal cavity. The word "permanent" is an expression of faith rather than fact: the ultimate goal is for these catheters to remain functional for as long the patients live or until they receive a transplant, but this is uncommon; many catheters have to be explanted and then replaced, primarily because of infection.

This invention relates to the field of catheter-related infection; in fact all percutaneous (through the skin) indwelling catheters have some degree of associated infection. Usually these infections are minor, sometimes they are dangerous and occasionally lethal, especially in immunocompromised patients. Irrespective of a particular subject's immunological status, indwelling percutaneous catheters carry with them the threat of clinical infection for 3 reasons: the breach in the skin; the catheter as a foreign body; imperfect fabrication of catheters.

The Breach in the skin: A hole through the skin partially occupied by a foreign body (catheter) is an obvious port of entry for microorganisms, which invariably take advantage of the situation. Usually, their progress is arrested within a few millimeters of the skin surface by various defence mechanisms, but not always: these "exit-site" infections around peritoneal catheters are the bane of all dialysis centers and frequently caused enforced explanation of catheters and their subsequent replacement.

The Catheter as a Foreign Body: A truly biocompatible material does not exist as yet and all catheters (and prostheses as well) are perceived by phagocytes as "foreign". In an attempt to destroy the catheter, phagocytes cluster around the object and expend their antimicrobial contents. Now degranulated, the phagocytes not only lose their microbiocidal capacity but they then play the role of hosts to viable microorganisms which are protected by the cell membranes from the actions of most antimicrobial drugs.

Catheter Material and Fabrication: Catheter materials fall broadly into 2 classes: hydrophilic and hydrophobic. This classification relates to the surfaces exposed to the bodily tissues, as often the bulk of a catheter is of one material, selected for desirable mechanical characteristics, and its surface coating is something entirely different.

Hydrophilic surfaces are composed of different materials such as PEG, PEO, PVP and others. The broad aim in applying these materials is to achieve a molecular similarity to the water-containing bodily tissues, which are recognized by defence mechanisms as "self": only partial success has been achieved in this endeavour by one of the inventors (U.S. Pat. Nos. 4,557,724 and 4,559,033) and many other investigators in this field. Bottle necked micropores and nanopores on the surface trap proteins which act as a substrate for deposition of precipitated calcium salts. Also, water, electrolytes and numerous other salts penetrate the hydrophilic material of the catheter surface, altering both its mechanical characteristics and its chemical structure, and the end result is a very adequate growth medium for microorganisms.

Analogous processes take place with hydrophobic surfaces: proteins attach through their hydrophobic segments, cholesterol and other lipid-soluble components of plasma also become attached and calcium salts are again precipitated. The main difference between the two types of catheters is that the biochemical soup is deposited on, rather than within, the surface of the hydrophobic catheters.

The first difficulty arises in recognizing that catheter surfaces, both internal and external, may harbor large numbers of bacteria or, less frequently, fungi. During the latent phase, microorganisms remain embedded, are difficult to obtain for diagnostic purposes and there are no clinical signs of infection. If any indwelling catheter remains in situ for long enough this equilibrium shifts, and always in the wrong direction: whether because of diversion of the host's defence mechanisms, a change in antimicrobial regimens or an increase in numbers and/or virulence of the embedded organisms, latent infections become overt.

It is known that correctly selected antimicrobial regimens, expecially when administered via the offending catheter, will sterilize its luminal contents and eliminate systemic infection. Most antimicrobial drugs will not eliminate microorganisms embedded in biofilms or in granule-depleted phagocytes, irrespective of laboratory reports on their sensitivities to a particular drug or drugs. A method is also needed for completely sterilizing the entire catheter.

In this regard it is also known that there are always some microorganisms associated with percutaneous catheters where the latter exit through the skin. When these microorganisms break through local defence mechanisms they migrate down the track of the catheter, form biofilms with the external surface and then there exists a similar situation as with internal catheter surfaces, except that there are no mechanical constraints to the organisms' migrating directly through surrounding tissues.

Mechanical solutions to some of these problems have been devised, the most familiar being the dacron cuffs in Tenckhoff- type peritoneal catheters, which are situated just under the skin and overlying the peritoneal membrane. These, and other similiar devices do offer partial solutions in that microorganisms are usually prevented from migrating along the catheter tracks. However, these same cuffs themselves frequently become infected and one of the inventors on this application has been associated with sufficient numbers of enforced catheter removals for this very reason, that alternative approaches were sought (U.S. Pat. Nos. 4,235,230 and 4,405,305).

Changing the catheter obviously resolves the immediate threat. Sometimes this is a simple procedure, sometimes it is technically difficult and sometimes it requires a formal surgical procedure for the (failed) permanent catheters. In this latter situation especially, catheters are maintained in position for as long as possible, occasionally too long, as a balanced risk.

Indwelling catheters are privileged sites for microorganisms, especially bacteria. Host phagocytes are stripped of their microbiocidal properties, there are physically protected niches with abundant nutrients in which the organisms may reside and, finally, bacteria may attach to catheters by producing a glycocalyx substrate which protects the embedded bacteria from the actions of antimicrobial drugs: this hybrid membrane existing mainly on the inside surface of catheters has recently been termed a biofilm.

The importance of biofilms located within indwelling catheters and causing recurrent infections has only been recognized in the last few years. These and other priviledged sites for microorganisms are responsible for many catheter explantations and systemic infections. Primarily associated with bacterial infections, there have appeared recently in the literature, reports that the resistance of biofilms to antimicrobial drugs can be greatly reduced by the application of electric currents: the presumed mechanism is that electric fields increase the permeability of bacteria and associated film structures to applied antimicrobial drugs. (ASAIO BOOK OF ABSTRACTS: March 1992).

Davis et al (U.S. Pat. No. 4,411,648) described electromotive, anti-infective treatments of bladder catheters and the bladder itself. Their stated aims were to sterilize the luminal fluid, urine, within the catheter and the urine in the bladder. To achieve these ends, two electrodes of opposite polarity traversed the length of the catheter and exited into the bladder and the electrodes were always in contact with an electrolyte (conductive) solution. One of the embodiments of Davis et al included two uninsulated electrodes running the length of the catheter and fixed to the walls. This arrangement was not aimed at, and could not achieve, eradication of infections associated with the catheter walls and respective biofilms, because:

1) The presence of two good conductors of electricity (the electrodes) in close opposition and electrically connected by another good conductor, the electrolyte solution(s), ensures that the great part of the electrical current and lines of force cross directly from one electrode to the other, which was the intention of the inventors who specified that the catheters were of non conductive material.

2) Leakage of current into associated biofilms with embedded bacteria will not penetrate those regions of biofilm which are coated by bodily lipophilic compounds.

3) The antimicrobial agents selected, heavy metals, although very effective in sterilizing liquids, (again the inventors intention) are of almost no value when applied to biological tissues: they precipitate immediately on contact.

It is emphasised that catheter based infections are an ever present threat, often disrupting effective medical regimens and sometimes killing patients and that conventional counter-measures may contain, but almost never eliminate, infectious organisms in any one catheter. There have been disclosed in several patent applications electromotive treatments of site specific pathologies of various internal organs in particular the bladder. Essentially, the techniques employed a tube (catheter) containing an electrode, which was inserted into, or in the region of, the target organ. However, with the exception of Davis et al and as for as the inventors are aware, no attempts were made by these various inventors to treat infections associated with catheters. Also, to the inventors knowledge, there have been no reports of any kind describing simultaneous treatments of both the internal and the external surfaces of an infected catheter by employing an electric field both to render the microorganisms more vulnerable and to accelerate administration rates of antimicrobial drugs.

SUMMARY OF THE INVENTION

It is a principal object of the invention to provide a novel method of treating recalcitrant infections associated with indwelling catheters.

It is a further object of the invention to render privileged bacteria and fungi, shielded within and upon the internal and external surfaces of indwelling catheters, more permeable to antimicrobial drugs by application of electric fields to said catheters.

It is another object of the invention to provide such a method wherein there is electromotive administration of antimicrobial drugs directly into catheter-associated sites shielding bacteria and fungi by means of said electric fields.

It is yet a further object of the invention to confine said electric fields within the immediate vicinity of said indwelling catheters by judicious siting of two electrodes of opposite polarity within and immediately without said indwelling catheter.

The above and other objects of the invention are achieved by specific embodiments which utilize electric fields to induce increased permeability simultaneously in the internal and external surfaces of indwelling catheters, in microorganismal biofilms, and in functionally deficient phagocytes harboring microorganisms, and to accelerate administration of antimicrobial drugs into said biofilms and phagocytes. In particular the above and other objects are achieved by a method of treating indwelling catheter associated infections which comprises the steps of:

- inserting into said indwelling catheter, through an end thereof exiting from a bodily area, a primary electrode;
- providing a secondary electrode-receptacle to be positioned on a skin area aroung the exit site of the catheter so as to surround at least a portion of said exiting end of the catheter;
- positioning the secondary electrode-receptacle on said skin area and sealing it to the skin and around a portion of the exiting end of the catheter so as to form a receptacle for holding liquids;
- infusing an aqueous solution into said catheter;
- instilling a solution of an antimicrobial drug into said secondary electrode-receptacle;
- applying a voltage differential between said primary and secondary electrode, whereby an electric field is applied to both internal and external surface of the catheter to drive any antimicrobial drug into contact with such surfaces.

The genesis of this invention arose from the understanding that effective treatment of catheter-based infections can be realized. This realization originated by the findings that:

When shielded by biofilms or within poorly functioning phagocytes, microorganisms display markedly increased resistance to antimicrobial drugs, including those to which they are supposedly sensitive, and that conventional systemic treatments are not effective in such cases;

All biological membranes and all hybrid membranes (biological+synthetic) become more permeable when electric fields are applied.

The electromotive force associated with electric fields accelerates the administration rates of all ionized solutes, including antimicrobial drugs.

The layering of indwelling catheter surfaces with electrically conductive hydrophilic and electrically resistive lipophilic tissue components is totally incoherent.

The desirability of confining the main intensity of applied electric fields to the indwelling catheter and immediately adjacent tissues.

Breached, and therefore damaged tissues, especially the skin, are less electrically resistive than are corresponding healthy tissues.

Based on the foregoing concepts, the following framework for the invention evolved.

All catheters relevant to this invention exit percutaneously or from the external urethral meatus. They have already been inserted previously for therapeutic purposes and have become infected with microorganisms.

Pertinent to this invention, indwelling catheters present two aspects, the internal surface and the external surface. Separated by millimeters only, each is almost totally isolated from the other and, even when harboring the same microorganisms, may give rise to entirely different disease states.

Electrically, the mammalian body consists of myriad resistors (or conductors) connected both in series and in parallel. In general terms, if the highly resistive outer layer of the skin ($>1$ Kohm), the stratum corneum, is avoided, the path of least resistance between two applied electrodes is the shortest distance through bodily tissues, whose average electrical resistance is about 50 $ohms/cm^3$.

The chaotic hydrophilic/lipophilic layering on catheter surfaces implies that many clusters of embedded microorganisms will be covered by, and sandwiched between, thin layers of electrically resistant lipids.

Except for certain spore forms, pathological bacteria and fungi, like their mammalian hosts, are approximately 70% water, which contains solutes electrically equivalent to about 1% sodium chloride. To survive and reproduce, microorganisms require some electrolytes and water in their immediate vicinity even if they have to supply the latter themselves by oxidative metabolism of substrates such as lipids: thus, the micro-environments of virulent microorganisms also demonstrate low electrical resistance.

Laboratory distilled water has an electrical resistance of $10^6$ $ohms/cm^3$ which is reduced only slightly by the addition of non-ionized solutes. Sodium chloride 1% and its electrolytic equivalents have an electrical resistance of 75 $ohms/cm^3$. Within the lumen of the catheters these values will be less because the configuration of the proposed electrodes will create an electrical matrix of resistances in parallel. Neverthless, there will still be orders of magnitude differences between the two types of solutions.

Treatments directed at eliminating microorganisms from both the internal and external surfaces of a catheter must be conducted over the same time frame. It is a truism that periodic bodily invasions by microorganisms will result in their eventual seeding in any implanted foreign body: treatment of the internal catheter surface only, will eventually result in reseeding by microorganisms which enter percutaneously along the external surface of the catheter.

The present invention involves a system whereby electrodes of opposite polarity are applied simultaneously to both the internal and external catheter surfaces. Preferably the different configurations of the primary internal electrode are so designed as to come into physical contact with different sections of the catheter surface as determined by the operator, both to provide direct electrical contact with the surface and also to disrupt mechanically the films of lipophilic compounds electrically shielding clusters of microorganisms. In addition, uninsulated core sections of the electrode will generate an electromotive force for accelerated administration of antimicrobial drugs from the lumen of the catheter into the surrounding internal catheter surface and its associated biofilms and functionally defective phagocytes.

A secondary electrode both to complete the electrical circuit and for simultaneous treatment of the external catheter surface is positioned over the catheter exit site so as to avoid the electrically resistant stratum corneum (which is breached at this site) and the current preferentially will travel along the tissues and body fluids surrounding the external surface of the catheter, or with a bladder catheter, through the external urethral meatus and along the urethra external to the catheter.

Thus, the shortest electrical pathway for this particular system is a circuit running from the primary electrode, into the catheter's internal surface and/or its luminal contents, around the tip of the catheter and back up its external surface and adjacent tissues to the secondary electrode and thence the voltage supply. Therefore, the maximum intensity of the electric field so generated is in and around the target site.

BRIEF DESCRIPTION OF THE DRAWINGS

Further characteristics and advantages of the inventions will become apparent from the description of the preferred but not exclusive embodiments of the device according to the invention, illustrated only by way of the non-limitative examples in the accompanying drawings, wherein.

DETAILED DESCRIPTION OF THE INVENTION

Primary Electrode

The primary electrode which has to be inserted inside a catheter has usually an elongated shape extending between a first extremity, which in use remains outside the catheter and a second, distal extremity, inserted in use, inside the catheter. Preferably only the terminal portion of the electrode located inside the catheter and comprising its distal extremity is electrically uninsulated and has a shape and size so as to physically contact portions of the inner surface of the catheter. The remaining part of the primary electrode, extending from said inner terminal portion up to its outer first extremity is electrically insulated.

Illustrative shapes of the terminal uninsulated portion of the primary electrode are a spiral or a filamentous configuration. In this latter case conductive filaments are attached and depart from a cylindrical or rod-like central body.

The sections of the uninsulated terminal portion of the electrode, which are in physical contact with the internal wall of the catheter are termed herein the periphery while the remainder of the portion of the electrode which is not physically contacting the catheter is termed the "core" section.

Figure 1:
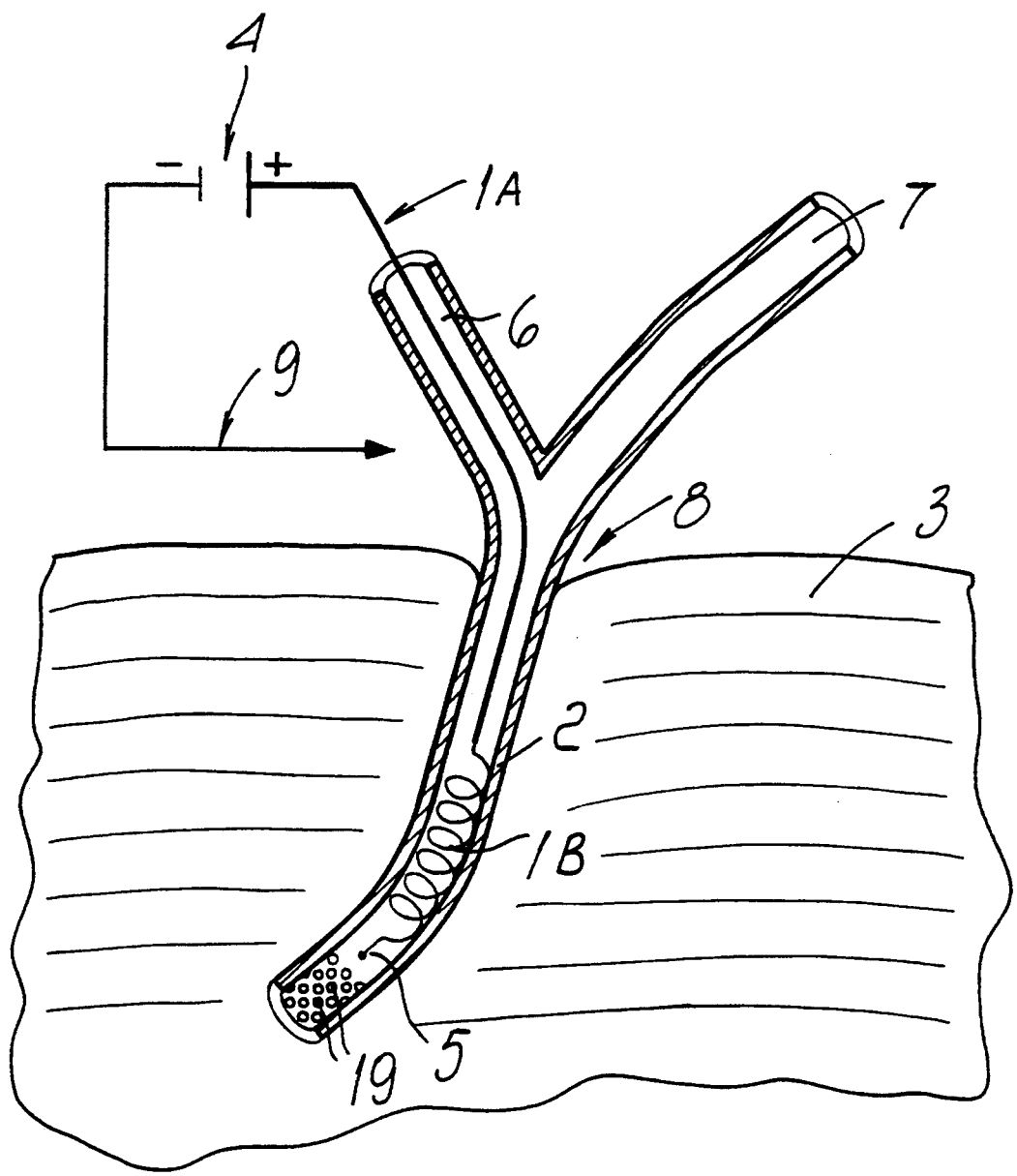
FIG. 1 is a schematic, sectional view of a first possible embodiment of the primary electrode according to the invention, positioned within a catheter which is inserted into a bodily area.
Figure 2:
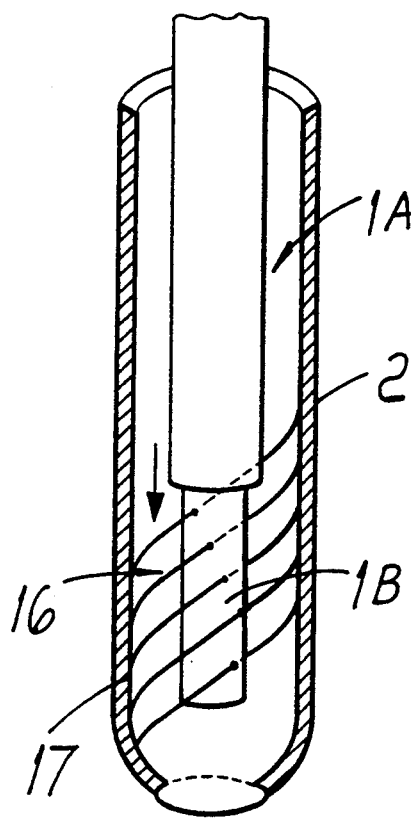
FIG. 2 is a schematic, sectional view in elevation of a further possible embodiment of the primary electrode inserted within a catheter.

Illustrative embodiments of the primary electrode are illustrated in FIG. 1 and FIG. 2 of the drawings.

With reference to FIG. 1 a primary electrode (1A–1B) has been located within a catheter (2) which is inserted into a bodily area (3). The primary electrode in this embodiment has a first insulated section (1A) which is electrically connected to the voltage source (4) and a second uninsulated inner terminal portion (1B) having a spiral shape of such a length that the distal extremity or tip (5) of the electrode does not protrude through the inner distal end of the indwelling catheter (2); the present invention also provides two access ports to be attached to the exterior port of the catheter: one (6) for the primary electrode and another (7) for infusion of fluids, At the distal portion of the catheter there are provided a plurality of holes (19) through which the solution infused into the catheter is able to be delivered to the external wall of the catheter. The skin around the exit site (8) of the catheter (2) is an area where bacterial infections may develop. In FIG. 1 there is further illustrated an electric wire (9) which connects the voltage source with the secondary electrode used in the method of the present invention and shown in FIG. 3. The spiral (1B) has an unconstrained diameter greater than the internal diameter of the catheter thereby tightly contacting its internal surface when inserted into the catheter.

With reference to FIG. 2, the primary electrode located within a catheter (2) comprises an insulated cylindrical portion (1A) protruding outside the catheter and a terminal uninsulated portion inside the catheter comprising a central cylindrical body (1B) and electrically conductive filaments (16) attached to, and protruding from the cylindrical body (1B). The filaments (16) are of flexible material, e.g. flexible spring wire, and have a length so as to be flexed against the inner surface of the catheter whereby maintaining a tight physical contact (17) therewith.

During the application of the primary electrode within a catheter the operator either advances or withdraws the primary electrode in a stepwise manner over the full length of the indwelling catheter while electrical current is running. The length of each separate movement (step) of the electrode during this procedure is approximately the length of the uninsulated distal portion of the electrode. The uninsulated spiral and filamentous sections of the electrode, which, as said, maintain at their periphery physical contact with the internal catheter surface, when moved through the length of the catheter, mechanically disrupt the thin films of electrically resistive lipids that shield some areas of biofilm. Direct electrical contact with most regions of the catheter surface is thereby ensured.

The electrode is preferably made of tempered stainless steel which posses all the desireable qualities of strength, resilience and durability and will form the major component of the electrodes. Insulation of the electrode from the voltage source to its uninsulated terminal portion e.g., the spiral filamentous sections is achieved by use for example of polymer coatings such as thermoretractible polyurethane. The surface of the uninsulated section remains stainless steel or is coated with a suitable conductive material deemed best at the fluid interface.

Fluids are infused through the catheter when an electric current is applied to the primary electrode sited in the catheter.

Infusion of a non-electrolyte in distilled water will create a high electrical resistance around the core section of the electrode so that the great proportion of the current will flow directly into the catheter surface via direct contact with the periphery of the electrode. Electric current, and hence electric fields, will be confined preferentially to the catheter surface because of its impregnated water and elecrolytes and so increase permeability of associated biofilms and phagocytes. This technique is employed in patients who are receiving systemic antimicrobial drugs, a fraction of which will also be within the catheter surface layers and is enabled to penetrate more readily the secluded microorganisms and their environs. Said antimicrobial drugs are the common ionised or non-ionised antimicrobial drugs, for example antibiotics used in the treatment of the infections caused by microorganisms, e.g., aminoglycosides (netilmycin . . . ) penicillins (penicillin 4, piperacillin) cephalosporin (cefoxitin, cefotaxime . . . ). The non-electrolytes selected are glucose, mannitol and glycine all of concentrations 3%–5%, and flow rates of the solutions down the catheters are 1–10 ml/min depending upon the internal volume of the catheter.

Infusion of an ionised antimicrobial drug of concentration $\geq 0.5\%$, ($\geq 10^{-2}$ molar) in distilled water constitutes a conductive medium within the lumen of the catheter. Electrical current will flow also from the core section of the electrode through the fluid infused in the catheter and will cause accelerated, iontophoretic administration of these same antimicrobial ions into the surface of the catheter, which is subjected to electric fields from both the core section and from the periphery of the electrode.

Electrical resistance continues to increase as antimicrobial concentrations decrease. Therefore, if the drugs are selected in concentrations $<0.5\%$ ($<10^{-2}$ molar) or if a non-ionised antimicrobial agent is chosen, a physiological electrolyte solution or a peritoneal dialysis solution—for peritoneal catheters only—is infused through the catheter so that drug administration into the surface of the catheter occurs by combined iontophoresis/electrophoresis or by electrophoresis. The electrolyte solutions used in such cases are usually physiological saline solutions.

Secondary Electrode-Receptacle

Figure 3:
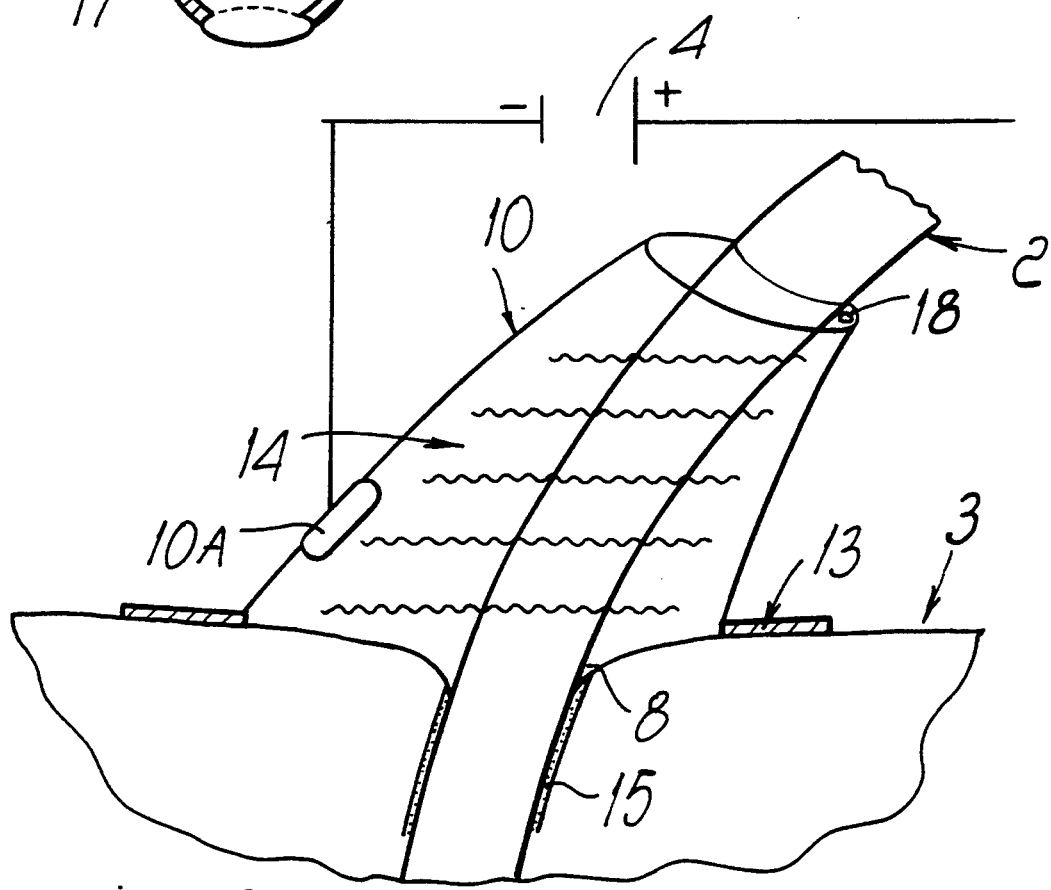
FIG. 3 is a schematic view of the secondary electrode-receptacle, according to the invention, which is connected to the voltage source.

FIG. 3 illustrates a secondary electrode-receptacle (10–10A) according to the present invention. It comprises a body of non-conductive material, for example of transparent polymer, having a cylindrical or, preferably a conical or truncated-conical shape. The receptacle (10) is positioned on a skin area around the exit site (8) o the catheter (2) from a bodily area (3) and surrounds part of the existing end of the catheter. It is sealed at the bottom to the skin by adhesive flanges (13) or any suitable adhesive material, such as plaster, tape, etc. At its top, the receptacle is sealed to the external surface of the exiting end of the catheter by any of the adhesive materials mentioned above. In this way a receptacle is formed capable of holding liquids.

A hole (18) provided on the top of the receptacle allows the introduction therein of antimicrobial drug solution (14).

On the wall of the receptacle there is applied a conductive element e.g. a metal plaque or a metal coating (10A) which contacts the liquid contained inside the receptacle (10) and which is connected with the voltage source (4) so as to form the secondary or counter electrode and to close the electrical circuit made of primary electrode 1A–1B, secondary electrode-receptacle (10–10A) and voltage source (4).

The therapeutic purpose of the secondary electrode—receptacle is to administer antimicrobial drugs through the exit site of the catheter and down the external surface of the catheter. The skin around the exit site of the catheter "dimples" inward: no synthetic material yet devised will promote its own attachment to stratum corneum.

Drug solutions of volumes 1–4 ml introduced into the receptacle (10) comprise ionised antimicrobial agents with concentration of $\geq 0.5\%$, ($\geq 10^{-2}$ molar) in distilled water, or ionised antimicrobial drugs of $<0.5\%$ ($<10^{-2}$ molar) concentration or non-ionised antimicrobial drugs in physiological electrolyte solutions.

The electrical parameters in the electric circuit formed between the voltage source, the primary and the secondary electrode and the solutions, vary according to this invention very widely, wherein the voltage ranges from 1 to 1300 Volts; the current varies from 400 $\mu$A to 6 Amps; the duty cycle varies from $1 \times 10^{-4}$:1 to 7:3, the application time period varies from 800 $\mu$s to 15 minutes and even up to 4 hours. The total electrical energy supplied varies to a lesser extent, ranging from 5–6 Joules to 340 Joules, when used in the treatment of bladder infections according to the present invention. Therefore for the purposes of the present invention, the total energy is limited to a range of 10 to 500 Joules administered at rates $\leq -1.5$ Watt/sec.

Polarities are applied as follows:

1. If the ionic charge on the systemically administered antimicrobial agent or the charge on the antimicrobial agent infused into the catheter, are of opposite sign to that of the antimicrobial drug in the secondary electrode-receptacle, then the polarity of the two electrodes is set to match those of the drugs they contact.
2. If the antimicrobial drug contacting one electrode is ionized and the drug contacting the second electrode is unionized, then the polarity applied to the ionized drug matches its charge.
3. If the antimicrobial agents contacting both electrodes are uncharged, then the selection of polarity is a matter of choice.
4. If the antimicrobial drugs contacting the two electrodes are both ionized and of the same charge, then the polarity is alternated at a frequency of once/minute to once/5 minutes.

It is to be understood that the above-described examples are only illustrative of the application of the present invention. Numerous modifications and alternative embodiments may be devised by those skilled in the art without departing from the spirit and scope of the present invention and the appended claims are intended to cover such modifications and arrangements.

We claim:

1. A method of treating indwelling catheter-based infections which comprises the steps of:
   providing two access ports on an exiting end at a catheter which exits from a bodily area;
   inserting into said indwelling catheter, through one said access port, a primary electrode;
   positioning a secondary electrode-receptacle on a skin area around the exit site of the catheter so as to surround at least a portion of said exiting end of the catheter, so as to form a receptacle for holding liquids;
   infusing an aqueous solution through a second one of said access ports and through said catheter;
   instilling an aqueous solution of an antimicrobial drug into said secondary electrode receptacle; and
   applying a voltage differential between said primary and secondary electrode, whereby an electric field is applied to both internal and external surfaces of the catheter to drive any antimicrobial drug into contact with such surfaces.

2. A method of treatment according to claim 1, wherein the step of inserting said primary electrode includes moving said primary electrode inside said catheter so as to mechanically disrupt any film deposit on the internal surface of the catheter.

3. A method of treatment according to claim 2, wherein the catheter associated infections are caused by microorganisms residing within priviledged sites which are attached to, and are within, the internal and external surface of said catheter.

4. A method of treatment according to claim 1, wherein said solution infused into said indwelling catheter comprises an ionized antimicrobial drug at a concentration greater than or equal to 0.50% w/v, in distilled water.

5. A method of treatment according to claim 1, wherein said solution infused into said indwelling catheter comprises an ionized antimicrobial drug at a concentration less than 0.50% w/v in a physiological electrolyte solution.

6. A method of treatment according to claim 1, wherein said solution infused into said indwelling catheter comprises a non-ionized antimicrobial drug in a physiological electrolyte solution.

7. A method of treatment according to claim 1, wherein said solution instilled into the secondary electrode-receptacle comprises an ionized antimicrobial drug at a concentration greater than or equal to 0.50% w/v, in distilled water.

8. A method of treatment according to claim 1, wherein said solution instilled into the secondary electrode-receptacle comprises an ionized antimicrobical drug at a concentration less than 0.50% w/v in a physiological electrolyte solution.

9. A method of treatment according to claim 1, wherein said solution instilled into said secondary electrode-receptacle comprises a non ionized antimicrobial drug in a physiological electrolyte solution.

10. A method of treatment according to claim 1, associated with systemic administration of antimicrobial drugs, wherein said aqueous solution infused through said indwelling catheter comprises non ionized solutes selected from glucose, mannitol, and glycine, in a concentration ranging from 3–5% w/v.

* * * * *